United States Patent [19]

Ueeda

[11] 3,975,407

[45] *Aug. 17, 1976

[54] METHOD FOR PRODUCING MALEIC ANHYDRIDE

[75] Inventor: Ryuhei Ueeda, Kurashiki, Japan

[73] Assignee: Kuraray Co., Ltd., Kurashiki, Japan

[ * ] Notice: The portion of the term of this patent subsequent to Sept. 16, 1992, has been disclaimed.

[22] Filed: May 14, 1975

[21] Appl. No.: 577,482

Related U.S. Application Data

[63] Continuation-in-part of Ser. No. 301,933, Oct. 30, 1972, Pat. No. 3,906,008.

[30] Foreign Application Priority Data

| | | |
|---|---|---|
| Nov. 2, 1971 | Japan | 46-88132 |
| Nov. 4, 1971 | Japan | 45-87780 |
| July 21, 1972 | Japan | 47-73548 |
| July 27, 1972 | Japan | 47-75252 |

[52] U.S. Cl. ................... 260/346.8 A; 252/437
[51] Int. Cl.$^2$ ............................. C07D 307/60
[58] Field of Search ........................ 260/346.8

[56] References Cited

UNITED STATES PATENTS 3,906,008   9/1975   Ueeda ........................... 260/346.8

*Primary Examiner*—Harry I. Moatz
*Attorney, Agent, or Firm*—Kaufman & Kramer

[57] ABSTRACT

Maleic anhydride is obtained by oxidizing an unsaturated hydrocarbon having at least 4 carbon atoms in the presence of a catalyst consisting essentially of the oxides of phosphorus and tungsten, with small amounts of a catalyst promoter selected from compounds of alkali metals, alkaline earth metals, copper, zinc, chromium, bismuth and titanium.

16 Claims, No Drawings

METHOD FOR PRODUCING MALEIC ANHYDRIDE

CROSS-REFERENCE TO RELATED APPLICATION

This is a continuation-in-part of application Ser. No. 301,933, filed Oct. 30, 1972 now U.S. Pat. No. 3,906,008.

This invention relates to a method for producing maleic anhydride by oxidizing an olefinic hydrocarbon having at least 4 carbon atoms or a hydrocarbon mixture containing such olefinic hydrocarbons with oxygen or a gaseous mixture containing oxygen.

It is well known that maleic anhydride can be produced by oxidizing an unsaturated hydrocarbon having at least 4 carbon atoms in the presence of a catalyst comprising vanadium oxide. However, when vanadium oxide is used as a catalyst, the yield of maleic anhydride is fairly low. In order to improve the yield of maleic anhydride when using a catalyst comprising vanadium oxide, co-catalysts such as molybdenum oxide, tungsten oxide and phosphorus oxide are generally added to the catalyst. For example, catalysts comprising vanadium pentoxide and oxides of phosphorus and tungsten are described in Japanese Pat. Publication No. 9688/62, and in French Pat. No. 1,260,597. In those cases, however, the yield of maleic anhydride is still unsatisfactory.

It is also known from British Patent specification No. 1,157,117 that maleic anhydride can be produced by oxidizing an unsaturated hydrocarbon of 4 or 5 carbon atoms using a catalyst comprising an oxide of molybdenum and an oxide of another metal, said metal being tin, antimony, iron or tungsten. A phosphorus or boron oxide may be used as a catalyst modifier or promoter. Here again, the yield of maleic anhydride is less than desirable.

It has now been found in accordance with the present invention, that by using tungsten as a catalyst component and phosphorus as a co-catalyst component, i.e., by using a catalyst system consisting essentially of the oxides of tungsten and phosphorus, it is possible to achieve high yields of maleic anhydride and to inhibit the formation of by-products such as acetic acid and aldehyde compounds. Surprisingly, it has been found that, when a vanadium compound which is generally used as the catalyst for the production of maleic anhydride is added to the catalyst system consisting essentially of oxides of tungsten and phosphorus, the resultant catalystic activity is unexpectedly hindered and the yield of maleic anhydride decreases.

It has now also been found that it is possible to obtain maleic anhydride in high yields and without a decrease in the catalytic activity during the reaction if there is added to the catalyst system consisting essentially of the oxides of tungsten and phosphorus, at least one catalyst promoter selected from the group consisting of alkali metal compounds, alkaline earth metal compounds, copper compounds, zinc compounds, chromium compounds, bismuth compounds and titanium compounds.

It has been found that it is possible to obtain maleic anhydride in high yields and without a decrease in the catalytic activity during the reaction by introducing a phosphorus compound into the reaction zone.

Catalyst systems comprising oxides of tungsten and phosphorus which are useful in the present invention include (1) mixtures containing an oxide of tungsten and an oxide of phosphorus, (2) complexes or compounds of tungsten, phosphorus and oxygen and (3) mixtures thereof. It is desirable that the atomic ratio of tungsten to phosphorus (W/P) be less than 30, and preferably range from 1 to 18.

In order to prepare the catalysts used in accordance with the present invention, there can be employed (1) a tungsten compound preferably selected from the group consisting of $WO_3$, $H_2WO_4$, $H_4WO_5$, $(NH_4)_2WO_4$, $W_4O_{11}$, $W_{10}O_{29}$, $WCl_6$, $WBr_6$, $WCl_5$, $WBr_5$, metatungstic acid, ammonium metatungstate, ammonium paratungstate, alkali metal tungstate, alkaline earth metal tungstate and the like; (2) a phosphorus compound preferably selected from the group consisting of phosphorus pentoxide, hydrophosphorous acid, phosphorous acid, diphosphorous acid, hypophosphoric acid, orthophosphoric acid, metaphosphoric acid, ultraphosphoric acid, an ammoniun salt of phosphorous or phosphoric acid, and the like. There can also be used compounds comprising by nature tungsten and phosphorus such as phosphotungstic acid or a salt thereof.

Catalyst promoters which are employed in the catalyst system of the present invention are compounds of alkali metals, alkaline earth metals, copper, zinc, chromium, bismuth and titanium. Such compounds include the oxides, hydroxides, nitrates, carbonates, sulfates, halides, acetates, phosphates and tungstates of alkali metals, alkaline earth metals, copper, zinc, chromium, bismuth and titanium. Also included as catalyst promoters within the scope of this invention are compounds which are converted to the aforementioned compounds upon calcination in air.

Typical alkali metal compounds which can be used include the oxides, hydroxides, chlorides, carbonates, sulfates, nitrates, phosphates, acetates, and the like of an alkali metal. When an alkali metal compound is employed with the catalyst consisting of oxides of phosphorus and tungsten, it is desirable that the atomic ratio of the alkali metal to phosphorus (alkali metal/phosphorus) in the catalyst range from about 0.001 to about 0.4. When the atomic ratio of alkali metal to phosphorus is more than 0.4, the initial activity of the catalyst decreases somewhat.

Typical alkaline earth metal compounds which can be used include the oxides, hydroxides, chlorides, carbonates, sulfates, nitrates, phosphates, acetates, and the like of an alkaline earth metal. When the alkaline earth metal compound is employed with the catalyst consisting of oxides of phosphorus and tungsten, it is desirable that the atomic ratio of the alkaline earth metal to phosphorus (alkaline earth metal/phosphorus) in the catalyst be in the range of from about 0.001 to about 100.

Typical copper compounds which can be used include cupric chloride, cuprous chloride, cupric sulfate, cuprous sulfate, cupric nitrate, cuprous nitrate, and the like. When a copper compound is employed with the catalyst consisting of oxides of phosphorus and tungsten, it is desirable that the atomic ratio of copper to phosphorus (Cu/P) in the catalyst range from about 0.0001 to about 2.0. When the atomic ratio is more than 2.0, the selectivity for maleic anhydride decreases.

Typical zinc compounds which can be used include zinc oxide, zinc chloride, zinc sulfate, zinc nitrate, and the like. When a zinc compound is employed with the catalyst consisting of oxides of phosphorus and tungsten, it is desirable that the atomic ratio of zinc to phosphorus (Zn/P) range from about 0.001 to about 1.0.

When the atomic ratio is more than 1.0, the conversion of olefinic hydrocarbons decreases.

Typical chromium compounds which can be used include chromium oxide, chromium chloride, chromium phosphate, chromium sulfate, chromic acid, and the like. When a chromium compound is employed with a catalyst consisting of oxides of phosphorus and tungsten, it is desirable that the atomic ratio of chromium to phosphorus (Cr/P) range from about 0.0001 to about 1.0. When the atomic ratio is more than 1.0, the selectivity for maleic anhydride decreases.

Typical bismuth compounds which can be used include bismuth nitrate, bismuth oxide, bismuth chloride, bismuth sulfate, and the like. When a bismuth compound is employed with a catalyst consisting of oxides of phosphorus and tungsten, it is desirable that the atomic ratio of bismuth to phosphorus (Bi/P) be in the range of from about 0.001 to about 100.

Typical titanium compounds which can be used include titanium dioxide, titanium nitrate, titanium sulfate, titanium trichloride, titanium tetrachloride, and the like. When a titanium compound is employed with a catalyst consisting of oxides of phosphorus and tungsten, it is desirable that the atomic ratio of titanium to phosphorus (Ti/P) be in the range of from about 0.001 to about 100.

The catalyst promoters described above can be used either singly or in combination of two or more.

When the aforementioned metal compounds are used in the form of chlorides or sulfates, chlorine or sulfate residues can remain in the catalyst. However, the presence thereof has no effect on catalytic activity.

In the present invention, phosphorus compounds can be introduced into the reaction zones by the following methods to maintain the high yield of maleic anhydride over extended periods: (1) a method wherein a phosphorus compound is added continuously or intermittently into the gaseous feed mixture, (2) a method wherein a phosphorus compound is introduced into the reaction zone with or without an inert gas such as steam, and (3) a method wherein a phosphorus compound is dissolved in a solvent such as water and is applied to the catalyst comprising oxides of tungsten and phosphorus during or after the reaction.

Typical phosphorus compounds which can be used include phosphine, phosphorus oxide (preferably phosphorus pentoxide), hydrophosphorous acid, phosphorous acid, diphosphorous acid, hypophosphoric acid, orthophosphoric acid, metaphosphoric acid, the salts of phosphorous or phosphoric acid which can be decomposed with heat such as ammonium dihydrogenphosphate, triethyl ammonium phosphate and organophosphorus compound preferably selected from the group consisting of

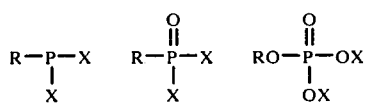

where R is phenyl or a lower alkyl radical and X is hydrogen or R, suitable compounds including for example diethyl phosphine, triethyl phosphine, tripropyl phosphine oxide, triethyl phosphate and triphenyl phosphate.

Typical methods for producing the catalyst are described below.

A tungsten compound, for example, is first calcined in an air stream at a temperature of 400° to 1000°C for 1 to 20 hours to obtain a tungsten oxide. Then, the tungsten oxide is mixed with phosphoric acid diluted with an adequate quantity of water and a catalyst promoter as described hereinabove, and then the mixture is heated to obtain a pastelike mixture. By molding the pastelike mixture to a desired size and drying, a catalyst can be obtained. Further, by calcining the thus obtained catalyst at a temperature of 300°C to 800°C, preferably 500°C to 700°C, more stable and active catalysts can be prepared.

The oxides of phosphorus and tungsten and a catalyst promoter as described hereinabove, which form the catalyst systems of the present invention can be supported on a carrier. In such case, supported catalyst systems can be obtained by the following method. After a molded carrier is dipped into an aqueous solution containing a tungsten compound or after a powdered carrier and tungsten are mixed and then molded into a desired size, the molded material is then calcined at an elevated temperature, and then the material is dipped into an aqueous solution containing a phosphorus compound and an aqueous solution containing a catalyst promoter as described hereinabove at the same time or separately. The supported catalyst obtained by such a method can be used in situ in the reaction. It can, of course, be used after being calcined. Conventional carriers can be employed such as silica gel, alumina, diatomaceous earth, alundum, carborundum, calcium sulfate, and the like. The olefinic hydrocarbons which can be used as feed materials according to the present invention are alkenes having at least 4 carbons, preferably 4 or 5 carbon atoms, and mixtures thereof. Typical feed materials are butene-1, butene-2, butadiene, cyclopentadiene, pentene-1, C$_4$-fractions obtained by naphtha cracking, and the like. It is possible to use mixtures of unsaturated hydrocarbons and hydrocarbon streams containing such olefinic hydrocarbons therein in the present invention.

When preparing maleic anhydride, the oxidizing agent employed can be oxygen or a gaseous mixture containing oxygen such as air in admixture with the aforementioned olefinic hydrocarbon. It is also possible to use, as an oxidizing agent, oxygen mixed with an inert gas such as nitrogen, carbon dioxide, steam, and the like. Furthermore, it is possible to use a dilute oxygen stream such as a portion of a reaction outlet gas stream containing oxygen. The concentration of olefinic hydrocarbons in a reaction gaseous mixture varies widely according to the species of the unsaturated hydrocarbon and the inert gas used for dilution. Generally, the molar ratio of olefinic hydrocarbon to oxygen is less than about 1/10 or more than about ½ in order to prevent explosions.

In order to produce maleic anhydride in accordance with the present invention, a catalyst containing oxides of phosphorus and tungsten and, if desired, a catalyst promoter as described hereinabove is packed into a reaction zone, and then a gaseous mixture containing an olefinic hydrocarbon and oxygen or oxygen-containing gas is introduced into the reaction zone. It is desirable that the gaseous hourly space velocity (S.V.) of the gaseous feed mixture be in the range of from 500 to 15,000 per hour, preferably from 1500 to 9000 per hour. It is desirable that the temperature, which is highest in the catalyst layer, range from 250°C to 650°C and preferably from 350°C to 500°C.

In the present invention, the catalyst can be used in the form of a fixed bed, a fluidized bed or a moving bed. It is preferable to use the catalyst in a fluidized bed or a moving bed, because the reaction for producing maleic anhydride is exothermic.

The invention will be described in more detail by the following examples which are intended only to illustrate the invention. Unless otherwise stated, all percentages and parts are by weight. In these examples, the terms of conversion, selectivity for maleic anhydride and yield are defined by the following equations:

$$\text{conversion} = \frac{\text{moles of reacted unsaturated hydrocarbon}}{\text{moles of unsaturated hydrocarbon charged to reactor}} \times 100$$

$$\text{selectivity} = \frac{\text{moles of maleic anhydride formed}}{\text{moles of unsaturated hydrocarbon reacted}} \times 100$$

$$\text{yield} = \text{conversion} \times \text{selectivity}$$

EXAMPLE 1

50 grams of tungstic acid was calcined in an air stream at a temperature of 800°C for 3 hours. 45 grams of the thus obtained tungstic oxide were mixed with an aqueous mixture containing 3.55 grams of phosphoric acid having a purity of 85% and 0.13 gram of lithium chloride to obtain a pastelike mixture. The pastelike mixture was molded, and then dried. The thus obtained catalyst had an atomic ratio of phosphorus: tungsten: lithium (P:W:Li) of 1:6.3:0.1. The catalyst was further calcined in an air stream at a temperature of 500°C for 3 hours before using in reaction.

The catalyst obtained by the aforementioned procedures was packed into a reactor having an inner diameter of 15 mm and a length of 60 cm, the reactor being equipped with testing means. Keeping the highest temperature in the catalyst layer at 460°C, air containing one volume percent of butene-1 was introduced into the reactor at a space velocity of 3000 per hour. The results are shown in Table 1.

Table 1

| Lapse of Time After Start of Reaction (hour) | conversion of butene-1 (%) | Yield (%) | | | | |
|---|---|---|---|---|---|---|
| | | Maleic Anhydride | Carbon Monoxide | Carbon Dioxide | Acetic Acid | Aldehyde Compounds |
| 3 | 98 | 49 | 32 | 15 | 0 | 2 |
| 15 | 98 | 52 | 31 | 12 | 1 | 2 |
| 60 | 98 | 48 | 32 | 15 | 0 | 3 |

EXAMPLE 2

45 grams of tungsten oxide which were obtained by the same procedures as in Example 1 was mixed with an aqueous mixture containing 3.55 grams of phosphoric acid having a purity of 85% and 0.33 gram of sodium chloride to obtain a pastelike mixture. The pastelike mixture was molded, and then dried. The thus obtained catalyst had an atomic ratio of phosphorus: tungsten: sodium (P:W:Na) of 1:6.3:0.1. The catalyst was further calcined in an air stream at a temperature of 500°C for 3 hours. Using the thus obtained catalyst, the same reaction procedures as in Example 1 were repeated. The results are shown in Table 2.

Table 2

| Lapse of Time After Start of Reaction (hour) | Conversion of butene-1 (%) | Yield (%) | | | | |
|---|---|---|---|---|---|---|
| | | Maleic Anhydride | Carbon Monoxide | Carbon Dioxide | Acetic Acid | Aldehyde Compounds |
| 3 | 94 | 58 | 26 | 9 | 0 | 1 |
| 15 | 90 | 55 | 24 | 9 | 0 | 2 |
| 60 | 91 | 59 | 21 | 8 | 0 | 1 |

EXAMPLE 3

The reaction procedures employed in Example 2 were repeated except that butadiene was used as the unsaturated hydrocarbon feed instead of butene-1. As a result, the yields of maleic anhydride after 3 hours, 15 hours and 50 hours from the start of reaction were 65%, 63% and 61%, respectively.

EXAMPLE 4

45 grams of tungsten oxide produced by the same procedure as in Example 1 was mixed with an aqueous mixture containing 3.55 grams of phosphoric acid having a purity of 85% and 0.2 gram of potassium carbonate to obtain a pastelike mixture. The pastelike mixture was subjected to the same treatments as in Example 1 to produce a catalyst. The catalyst had an atomic ratio of phosphorus: tungsten: potassium (P:W:K) of 1:6.3:0.1. Using the catalyst, the same reaction procedure as in Example 1 was repeated. The deterioration in yield of maleic anhydride with time is shown in Table 3.

Table 3

| Lapse of Time After Start of Reaction (hour) | Conversion of butene-1 (%) | Yield (%) | | | | |
|---|---|---|---|---|---|---|
| | | Maleic Anhydride | Carbon Monoxide | Carbon Dioxide | Acetic Acid | Aldehyde Compounds |
| 3 | 96 | 65 | 21 | 9 | 0 | 1 |
| 15 | 95 | 62 | 20 | 11 | 0 | 2 |
| 60 | 95 | 63 | 20 | 11 | 0 | 1 |

EXAMPLE 5

Using a catalyst which was obtained by the same procedure as in Example 2 except that the amount of sodium chloride employed was changed, the same reaction procedures as in Example 2 were repeated. The results are shown in Table 4.

Table 4

| No. | Na/P (atomic ratio) in the Catalyst | Conversion of Butene-1 (%) | Yield of Maleic Anhydride (%) |
|---|---|---|---|
| I | 0.05 | 98 | 54 |
| II | 0.10 | 98 | 56 |
| III | 0.25 | 85 | 48 |
| IV | 0.50 | 12 | 4 |
| V | 1.00 | 8 | 2 |

When the atomic ratio of alkali metal/phosphorus was more than 0.4, the activity of the catalyst decreased dramatically.

EXAMPLE 6

The same reaction procedures as in Example 2 were repeated except that a gaseous mixture consisting of 25 weight percent of butenes, 48 weight percent of n-butene and 27 weight percent of isobutene was used instead of butene-1. As a result, the yields of maleic anhydride after 3 hours, 15 hours and 50 hours from the start of the reaction were 33%, 35% and 33%, respectively.

EXAMPLE 7

50 grams of tungstic acid was calcined in an air stream at a temperature of 800°C for 3 hours. 45 grams of the obtained tungsten oxide was mixed with an aqueous mixture containing 7.0 grams of phosphoric acid having a purity of 85% and 0.58 gram of anhydrous magnesium chloride to obtain a pastelike mixture and then the pastelike mixture was molded and dried. The atomic ratio of phosphorus: tungsten: magnesium (P:W:Mg) in the thus obtained catalyst was 1:3.2:0.1. The catalyst was further calcined in an air stream at a temperature of 500°C for 2 hours before using in the reaction.

Using the aforementioned catalyst, the same reaction procedures as in Example 1 were repeated. The results are shown in Table 5.

Table 5

| Lapse of Time After Start of Reaction (hour) | Conversion of butene-1 (%) | Yield (%) | | | | |
|---|---|---|---|---|---|---|
| | | Maleic Anhydride | Carbon Monoxide | Carbon Dioxide | Acetic Acid | Aldehyde Compounds |
| 3 | 98 | 51 | 27 | 17 | 1 | 2 |
| 15 | 98 | 52 | 28 | 15 | 1 | 2 |
| 60 | 97 | 49 | 30 | 14 | 1 | 3 |

EXAMPLE 8

45 grams of tungsten oxide which was produced by the same method as in Example 7 was mixed with an aqueous mixture containing 7.0 grams of phosphoric acid having a purity of 85% and 1.5 grams of barium chloride dihydrate to obtain a pastelike mixture. The pastelike mixture was molded, and then dried. The atomic ratio of phosphorus: tungsten: barium (P:W:Ba) in the thus obtained catalyst was 1:3.2:0.1. The catalyst was further calcined in an air stream at a temperature of 500°C for 3 hours before using in the reaction.

Using the catalyst, the same reaction procedures as in Example 7 were repeated. The results are shown in Table 6.

Table 6

| Lapse of Time After Start of Reaction (hour) | Conversion of butene-1 (%) | Yield (%) | | | | |
|---|---|---|---|---|---|---|
| | | Maleic Anhydride | Carbon Monoxide | Carbon Dioxide | Acetic Acid | Aldehyde Compounds |
| 3 | 94 | 54 | 28 | 10 | 0 | 2 |
| 15 | 94 | 48 | 24 | 8 | 1 | 1 |
| 60 | 91 | 48 | 26 | 9 | 0 | 2 |

EXAMPLE 9

45 grams of tungsten oxide which were obtained by the same method as in Example 7 was mixed with an aqueous mixture containing 7.0 grams of phosphoric acid having a purity of 85% and 14.8 grams of barium chloride dihydrate to obtain a pastelike mixture. The pastelike mixture was molded, and then dried. The atomic ratio of phosphorus: tungsten: barium (P:W:Ba) in the thus obtained catalyst was 1:3.2:1. The catalyst was further calcined in an air stream at a temperature of 500°C for 3 hours before using in the reaction.

Using this catalyst, the same reaction procedures as in Example 7 were repeated. The results are shown in Table 7.

Table 7

| Lapse of Time After Start of Reaction (hour) | Conversion of butene-1 (%) | Yield (%) | | | | |
|---|---|---|---|---|---|---|
| | | Maleic Anhydride | Carbon Monoxide | Carbon Dioxide | Acetic Acid | Aldehyde Compounds |
| 3 | 97 | 52 | 28 | 12 | 0 | 5 |
| 15 | 98 | 56 | 29 | 9 | 1 | 3 |
| 60 | 94 | 55 | 28 | 9 | 0 | 2 |

EXAMPLE 10

Mixtures consisting of 45 grams of tungsten oxide and 7.0 grams of phosphoric acid having a purity of 85% were mixed with calcium sulfate dihydrate in amounts shown in Table 8, and then catalysts were produced from the respective mixtures by the same procedure as in Example 7.

Using these catalysts, the same reaction procedures as in Example 7 were repeated. The results are shown in Table 8.

Table 8

| No. | Quantity of Calcium Sulfate Dihydrate (g) | Atomic Ratio of Ca/P | Yield of Maleic Anhydride (%) | | |
|---|---|---|---|---|---|
| | | | After 3 hours | After 30 hours | After 60 hours |
| I | 1.0 | 0.1 | 58 | 54 | 57 |
| II | 5.2 | 0.5 | 62 | 58 | 59 |
| III | 10.4 | 1.0 | 57 | 60 | 54 |
| IV | 20.8 | 2.0 | 59 | 59 | 54 |

EXAMPLE 11

A catalyst was prepared from 45 grams of tungsten oxide, 7 grams of phosphoric acid having a purity of 85% and 0.7 gram of calcium chloride anhydrate by the same method as in Example 7. The atomic ratio of phosphorus: tungsten: calcium (P:W:Ca) in the catalyst was 1:3.2:0.1. The catalyst was treated with air at a temperature of 500°C for 3 hours before using in the reaction. Using this catalyst, the same reaction procedures as in Example 7 were repeated except that butadiene was used instead of butene-1. The results are shown in Table 9.

Table 9

| Lapse of Time After Start of Reaction (hour) | Conversion of Butadiene (%) | Yield (%) | | | | |
|---|---|---|---|---|---|---|
| | | Maleic Anhydride | Carbon Monoxide | Carbon Dioxide | Acetic Acid | Aldehyde Compounds |
| 3 | 99 | 66 | 16 | 11 | 5 | 1 |
| 15 | 99 | 65 | 17 | 12 | 4 | 1 |
| 60 | 100 | 63 | 17 | 14 | 3 | 3 |

EXAMPLE 12

Using the same catalyst as used in Example 11, the same reaction procedures as in Example 7 were repeated except that a mixture consisting of 25 weight percent of butene, 48 weight percent of n-butene and 27 weight percent of isobutene was used instead of butene-1. The yield of maleic anhydride after 3 hours, 15 hours and 60 hours from the start of reaction were 31%, 34% and 34%, respectively.

EXAMPLE 13

45 grams of tungsten oxide, 5 grams of phosphoric acid having a purity of 85%, 1.0 gram of cuprous chloride and a sufficient quantity of water were mixed to obtain a pastelike mixture. The pastelike mixture was molded and dried, and then calcined in an air stream at a temperature of 500°C for 2 hours.

Using the aforementioned catalyst, the same reaction procedures as in Example 1 were repeated. The results are shown in Table 10.

Table 10

| Lapse of Time After Start of Reaction (hour) | Conversion of Butene-1 (%) | Yield of Maleic Anhydride (%) |
|---|---|---|
| 3 | 98 | 58 |
| 15 | 98 | 59 |
| 60 | 98 | 60 |

EXAMPLE 14

Catalyst (I)-(IX) below were prepared in accordance with the same method as described in Example 13 from 45 grams of tungsten oxide, phosphoric acid having a purity of 85% in the amount shown in Table 11 and a catalyst promoter, each name and the amount of which are shown in Table 11.

Table 11

| Catalyst | Tungsten Oxide (g) | Phosphoric Acid Having a Purity of 85% (g) | Catalyst Promoter (g) | Atomic Ratio |
|---|---|---|---|---|
| I | 45 | 7 | Zinc chloride - 0.8 | W/P/Zn = 1/0.31/0.15 |
| II | 45 | 7 | Chromium nitrate - 2.4 | W/P/Cr = 1/0.31/0.05 |
| III | 45 | 7 | Bismuth nitrate - 2.9 | W/P/Bi = 1/0.31/0.001 |
| IV | 45 | 7 | Titanium tetrachloride - 1.2 | W/P/Ti = 1/0.31/0.33 |
| V | 45 | 7 | Titanium trichloride (purity 20%) - 23 | W/P/Ti = 1/0.31/0.15 |
| VI | 45 | 3.5 | Titanium dioxide - 24 + Titanium trichloride (purity 20%) - 0.23 | W/P/Ti = 1/0.16/1.6 |
| VII | 45 | 3.5 | Titanium dioxide - 48 + Tatanium trichloride (purity 20%) - 0.23 | W/P/Ti = 1/0.16/3.2 |
| VIII | 45 | 7 | Bismuth nitrate pentahydrate - 15 | W/P/Bi = 1/0.31/0.5 |
| IX | 45 | 2.2 | Bismuth nitrate pentahydrate - 94 | W/P/Bi = 1/0.10/1 |

Using catalysts (I) – (IX), the same reaction procedure as in Example 13 were repeated. The results are shown in Table 12.

Table 12

| Catalyst | Conversion of Butene-1 (%) | | | Yield of Maleic Anhydride (%) | | |
|---|---|---|---|---|---|---|
| | After 3 Hours | After 15 Hours | After 60 Hours | After 3 Hours | After 15 Hours | After 60 Hours |
| I | 95 | 94 | 95 | 59 | 57 | 54 |
| II | 100 | 100 | 100 | 52 | 50 | 51 |
| III | 91 | 90 | 90 | 54 | 53 | 50 |
| IV | 100 | 100 | 100 | 64 | 60 | 64 |
| V | 99 | 99 | 99 | 63 | 62 | 60 |
| VI | 82 | 80 | 80 | 58 | 58 | 59 |
| VII | 79 | 75 | 74 | 57 | 57 | 56 |
| VIII | 80 | 81 | 80 | 48 | 50 | 54 |
| IX | 75 | 72 | 72 | 42 | 40 | 44 |

EXAMPLE 15

A catalyst which was prepared from 45 grams of tungsten oxide and 7.0 grams of phosphoric acid having a purity of 85% and 0.8 grams of zinc chloride was packed in a reactor having an inner diameter of 15 millimeters and a length of 600 millimeters. The reactor was equipped with means for treating and a sprayer was adapted to spray phosphoric acid into the reactor. Air containing 1 volume percent of butene-1 introduced into the reactor at a space velocity of 3000 per hour and an aqueous solution containing 10 weight percent of triammonium phosphate was sprayed into the reactor at a rate of 2 grams per day.

The yields of maleic anhydride after 3 hours, 30 hours and 300 hours from the start of reaction were 59%, 63% and 63%, respectively.

EXAMPLE 16

Catalyst (I) and (II) below were prepared in accordance with the same method as described in Example 13 from 45 grams of tungsten oxide, 3.55 grams of phosphoric acid having a purity of 85% and a catalyst promotor, each name and the amount of which are shown in Table 13.

Table 13

| Catalyst | WO₃ g | H₃PO₄(85%)g | Stabilizer |
|---|---|---|---|
| I | 45 | 3.55g | Potassium carbonate 0.1 Calcium chloride anhydride 0.24 |
| II | 45 | 3.55g | Titanium tetrachloride 1.2 Zinc chloride 0.4 |

The thus obtained catalysts were packed in the reactor having an inner diameter of 15 millimeters and a length of 50 centimeters. Maintaining the highest temperature in the catalyst layer at 490°C., air containing one volume percent of butene-1 was introduced into the reactor at a space velocity of 3000 per hours. The results are shown in Table 14.

Table 14

| Catalyst | Lapse of Time after start of reaction (hr) | Conversion of butene-1 (%) | Yield of maleic anhydride (%) |
|---|---|---|---|
| I | 3 | 98 | 62 |
| | 15 | 94 | 61 |
| | 60 | 95 | 62 |
| II | 3 | 98 | 60 |
| | 15 | 98 | 61 |
| | 60 | 98 | 60 |

EXAMPLE 17

Mixtures consisting of 45 grams of tungsten oxide and 7.0 grams of phosphoric acid having a purity of 85% were mixed with calcium sulfate dihydrate in amounts shown in Table 15, and three catalysts were produced from the respective mixtures by the same procedure as in Example 7.

Using these catalysts, the reaction procedures of Example 1 were used, except that the reaction temperature was raised somewhat and the air containing butene-1 was introduced into the reactor at a space velocity of 1500 per hour. The results are shown in Table 15.

Table 15

| No. | Quantity of calcium sulfate dihydrate (g) | Atomic Ratio of Ca/P | Reaction Temperature °C. | Yield of Maleic Anhydride (%) | | |
|---|---|---|---|---|---|---|
| | | | | After 3 hrs. | After 30 hrs. | After 60 hrs. |
| I | 0.1 | 0.01 | 490 | 60 | 58 | 58 |
| II | 42.0 | 4.0 | 510 | 57 | 57 | 57 |
| III | 83.0 | 8.0 | 510 | 54 | 53 | 53 |

What is claimed is:

1. A method for preparing maleic anhydride which comprises oxidizing a gaseous mixture containing an olefinic hydrocarbon having 4 or 5 carbon atoms or a hydrocarbon mixture thereof and oxygen or an oxygen-containing gas in a reaction zone in the presence of a catalyst consisting essentially of the oxides of tungsten and phosphorus, the atomic ratio of tungsten to phosphorus being less than 30, and at least one catalyst promoter selected from the group consisting of compounds of alkali metals, alkaline earth metals, alkaline earth metals, copper, zinc, chromium, bismuth and titanium at a temperature in the range of from 250°C. to 650°C.

2. A method according to claim 1 in which the catalyst promoter is selected from (I) the oxides, hydroxides, nitrates, carbonates, sulfates, halides, acetates, phosphates and tungstates of alkali metals, alkaline earth metals, copper, zinc, chromium, bismuth and titanium, and (II) compounds which are converted to (I) upon calcination in air.

3. A method according to claim 2 wherein there is introduced into the reaction zone an additional compound selected from the group consisting of phosphine, phosphorus oxides, hydrophosphorous acid, phosphorous acid, diphosphorous acid, hypophosphoric acid, orthophosphoric acid, metaphosphoric acid, salts of phosphorous and phosphoric acid which are decomposed at the reaction temperature, and organophosphorus compounds of the formulae:

and

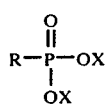

wherein R is phenyl or lower alkyl and X is hydrogen or R.

4. A method according to claim 2 wherein the catalyst is supported on a carrier.

5. A method according to claim 1 wherein the catalyst consists essentially of a complex or a compound of tungsten, phosphorus and oxygen.

6. A method according to claim 1 wherein the catalyst consists essentially of oxides of tungsten and phosphorus, a complex or a compound of tungsten, phosphorus and oxygen, and mixtures thereof.

7. A method according to claim 1 wherein oxidation is effected by admixing said olefinic hydrocarbon with an oxidizing agent comprising oxygen or an oxygen-containing gas.

8. A method according to claim 6 wherein the molar ratio of olefinic hydrocarbon to oxygen is less than 1/10 or more than ½.

9. A method according to claim 1 wherein the gaseous hourly space velocity through the reaction zone ranges from 500 to 15,000 per hour.

10. A method according to claim 2 in which the catalyst promoter is selected from the group consisting of the oxides, hydroxides, chlorides, carbonates, sulfates, nitrates, phosphates and acetates of an alkali metal, the atomic ratio of the alkali metal to phosphorus ranging from about 0.001 to about 0.4.

11. A method according to claim 2 in which the catalyst promoter is selected from the group consising of the oxides, hydroxides, chlorides, carbonates, sulfates, nitrates, phosphates and acetates of an alkaline earth metal, the atomic ratio of the alkaline earth metal to phosphorus ranging from about 0.001 to about 100.

12. A method according to claim 2 in which the catalyst promoter is selected from the group consisting of cupric chloride, cuprous chloride, cupric sulfate, cuprous sulfate, cupric nitrate and cuprous nitrate, the atomic ratio of copper to phosphorus ranging from about 0.001 to about 2.0.

13. A method according to claim 2 in which the catlayst promoter is selected from the group consisting of zinc oxide, zinc chloride, zinc sulfate and zinc nitrate, the atomic ratio of zinc to phosphorus ranging from about 0.001 to about 1.0.

14. A method according to claim 1 in which the catalyst promoter is selected from the group consisting of chromium oxide, chromium chloride, chromium phosphate, chromium sulfate and chromic acid, the atomic ratio of chromium to phosphorus ranging from about 0.001 to about 1.0.

15. A method according to claim 2 in which the catalyst promoter is selected from the group consisting of bismuth nitrate, bismuth oxide, bismuth chloride and bismuth sulfate, the atomic ratio of bismuth to phosphorus ranging from about 0.001 to about 100.

16. A method according to claim 2 in which the catalyst promoter is selected from the group consisting of titanium dioxide, titanium nitrate, titanium sulfate, titanium trichloride and titanium tetrachloride, the atomic ratio of titanium to phosphorus ranging from about 0.001 to about 100.

* * * * *

PO-1050
(5/69)

UNITED STATES PATENT OFFICE
CERTIFICATE OF CORRECTION

Patent No. 3,975,407   Dated 8/17/76

Inventor(s) Ryuhei Veeda; Kurashiki Japan

It is certified that error appears in the above-identified patent and that said Letters Patent are hereby corrected as shown below:

In Claim 1, lines 10-11, delete the second occurrence of "alkaline earth metals";

In Claim 11, line 2, "consising" should read --consisting--.

Signed and Sealed this

Eleventh Day of January 1977

[SEAL]

Attest:

RUTH C. MASON
Attesting Officer

C. MARSHALL DANN
Commissioner of Patents and Trademarks